United States Patent [19]

Nash et al.

[11] Patent Number: 5,578,041

[45] Date of Patent: Nov. 26, 1996

[54] EXTERNAL FIXATION DEVICE

[75] Inventors: Ronald A. Nash, Silver Springs, N.Y.; David M. Nunamaker, West Grove, Pa.

[73] Assignee: Trustees of the University of Pennsylvania, Philadelphia, Pa.

[21] Appl. No.: 323,135

[22] Filed: Oct. 14, 1994

[51] Int. Cl.$^6$ .............................. A61B 17/64; A61B 17/10
[52] U.S. Cl. .................................. 606/54; 606/59; 606/76
[58] Field of Search .................................. 606/54, 55, 56, 606/57, 58, 59, 60, 73, 76

[56] References Cited

U.S. PATENT DOCUMENTS

| | | |
|---|---|---|
| 3,470,873 | 10/1969 | Walker et al. . |
| 3,877,424 | 4/1975 | Murray . |
| 4,029,090 | 6/1977 | Dawson, Jr. . |
| 4,185,624 | 1/1980 | Gentile ........................................ 606/73 |
| 4,320,722 | 3/1982 | Glassman et al. . |
| 4,604,996 | 8/1986 | Nunamaker et al. . |
| 5,087,258 | 2/1992 | Schewior ................................... 606/56 |
| 5,112,331 | 5/1992 | Miletich .................................... 606/59 |

OTHER PUBLICATIONS

Reprinted from *Veterinary Surgery*, Sep.–Oct. 1986, vol. 15, No. 5, "A New External Skeletal Fixation Device That Allows Immediate Full Weightbearing Application in the Horse" by D. M. Nunamaker, VMD DiplomateA VCS, D. W. Richardson, DVW, DiplomateA VCS, D. M. Butterweck, BSE, M. T. Provost, BSCSE, and R. D. Sigafoos.
"External Skeletal Fixation in the Horse" by D. M. Nunamker, VMD and D. W. Richardson, DVM.
Product Data Sheet from Fiber Resin Corp. for FR–1177, "ULTRACAST.".
Product Information Sheet from BJB Enterprises for TC–880 A/B, Rigid 80 Shore D Urethane Casting System.
Product Information Sheet from BJB Enterprises for TC–806 A/B, Urethane Casting System–White.
Product Information Sheet from BJB Enterprises for TC–804 A/B, Urethane Casting System–White.

*Primary Examiner*—Michael Powell Buiz
*Assistant Examiner*—Scott Markow
*Attorney, Agent, or Firm*—Ratner & Prestia

[57] ABSTRACT

The present invention provides an external skeletal fixator for treating an injured mammalian limb. The fixator has a plurality of transfixation pins which pass through the intact bone of the injured limb proximal to the injured bone. These pins extend beyond the outer edges of the intact bone. These pins are supported by support members which abut the intact bone, extending through the soft tissue. These support members are, in turn, supported by a superstructure capable of supporting the weight of the animal, which superstructure extends beyond the distal end of the injured limb. Thus in the case of a weight bearing limb, the weight of the animal is transferred from the intact bone to the pins, to the supporting members, to the superstructure, to the ground, thus bypassing the injured bone.

20 Claims, 4 Drawing Sheets

EXTERNAL FIXATION DEVICE

BACKGROUND OF THE INVENTION

1. Field of the Invention

The present invention relates to apparatus and methods for treating injuries to bones in mammals, especially injuries to weight-bearing bones. Specifically, this invention relates to external fixation devices for immobilizing a limb or portion of a limb while allowing use of the limb as a weight bearing limb.

2. Description of the Related Art

Injuries to the limbs of mammals, including animals and man, are generally treated by immobilizing the limb until the injury heals. One method commonly used in man and certain other mammals is to immobilize the limb in a hard cast, generally formed of plaster or fiberglass. While the use of such a cast is convenient and effective, casts have disadvantages as well.

First, an injured limb is most often swollen after a break occurs. Placing the limb in a cast will create undue pressure on the swollen limb. Further, as the swelling abates, the cast can become loose, necessitating its removal and reapplication. Further, if the injured limb has superficial lacerations or other injuries, a cast will effectively prevent proper treatment. Plaster or fiberglass casts are also bulky and cumbersome, as well as uncomfortable. Finally, such casts can support only a limited amount of weight. While a man may use such a cast effectively, the cast will be unable to support the weight of larger animals. This is especially true where the animal is not intelligent and will continue to try to use the injured limb as normal.

Attempts to overcome these disadvantages have been made. For example, Walker, U.S. Pat. No. 3,470,873, discloses an adjustable splint which is said to be especially useful to immobilize the injured leg of a bovine animal. The Walker splint includes a pivoting plate to which the foot of the animal is attached, and the animal can walk about with the splint in place. Dawson, U.S. Pat. No. 4,029,090, describes a heavy, hinged framework which can be employed to encase the injured foreleg of a horse. Application of the brace allows the horse to stand but causes rub sores. A simple brace for an equine animal's injured leg, including a support for the hoof, is disclosed in U.S. Pat. No. 4,320,722 to Glassman, et al. Like a plaster cast, these devices are designed to support the entire weight of the animal, through the device, on soft tissues. Especially in the case of a large animal, this is impractical and undesirable. The soft tissue is subject to abrasion from the device, causing open sores to develop, as well as bruising. Pressure on the soft tissues from the device can also lead to the formation of decubitus ulcers which are difficult to treat and, if left untreated can eventually lead to bone loss in affected areas.

External fixation devices which transfer stress directly to bone have also been developed to try to overcome the disadvantages of the prior devices. In U.S. Pat. No. 3,877,424 to Murray, pins are inserted through bone fragments and extend beyond the surrounding soft tissue, where they are bonded to a rigid bridge. However, the Murray fixator makes no provision to allow full weight bearing on the injured limb. Thus it is not useful where the patient is not intelligent and will continue to use the limb, as in bovine, equine, and other veterinary applications.

Finally, U.S. Pat. No. 4,604,996 to Nunamaker, et al., which is incorporated herein by reference, discloses a device for transferring the full weight bearing force of an animal directly to an external fixation device. The device uses pins which pass through the bone proximal the injured bone in the injured limb of the animal. These pins are then secured to a superstructure which transfers the weight of the animal from the pins to the ground. This device retains several shortcomings.

First, the stress placed on the pins in the Nunamaker device increases as the distance from the bone to the superstructure increases. Since the superstructure cannot be placed directly against the bone of the patient, the stress on the pins is very high. In Nunamaker, this is overcome by providing larger pins which are more likely to withstand the stress placed upon them and by providing more pins. Both of these features leads to further problems. Larger pins require that larger holes be made in the intact bone. Larger holes act as larger stress concentrators, leading to a greater chance of bone fracture. Additional pins complicate this. Thus, it is one object of this invention to provide apparatus and a method of using it which are effective for treating an injured mammalian limb, while avoiding the problems recited above. It is another objective that the treated limb be capable of supporting the mammal's full weight immediately after application of the apparatus without reliance on soft tissue support.

SUMMARY OF THE INVENTION

The present invention provides an external skeletal fixator for treating an injured mammalian limb. The fixator has a plurality of transfixation pins which pass through the intact bone of the injured limb proximal to the injured bone. These pins extend beyond the outer edges of the intact bone. These pins are supported by support members which abut the intact bone, extending through the soft tissue. These support members are, in turn, supported by a superstructure capable of supporting the weight of the animal, which superstructure extends beyond the distal end of the injured limb. Thus in the case of a weight bearing limb, the weight of the animal is transferred from the intact bone to the pins, to the supporting members, to the superstructure, to the ground, thus bypassing the injured bone.

DETAILED DESCRIPTION OF THE DRAWINGS

This invention will be described based upon its application to horses, but the invention can be applied any mammal (as well as some non-mammals). The principles set forth herein with respect to horses apply equally well to other animals.

Figure 7:
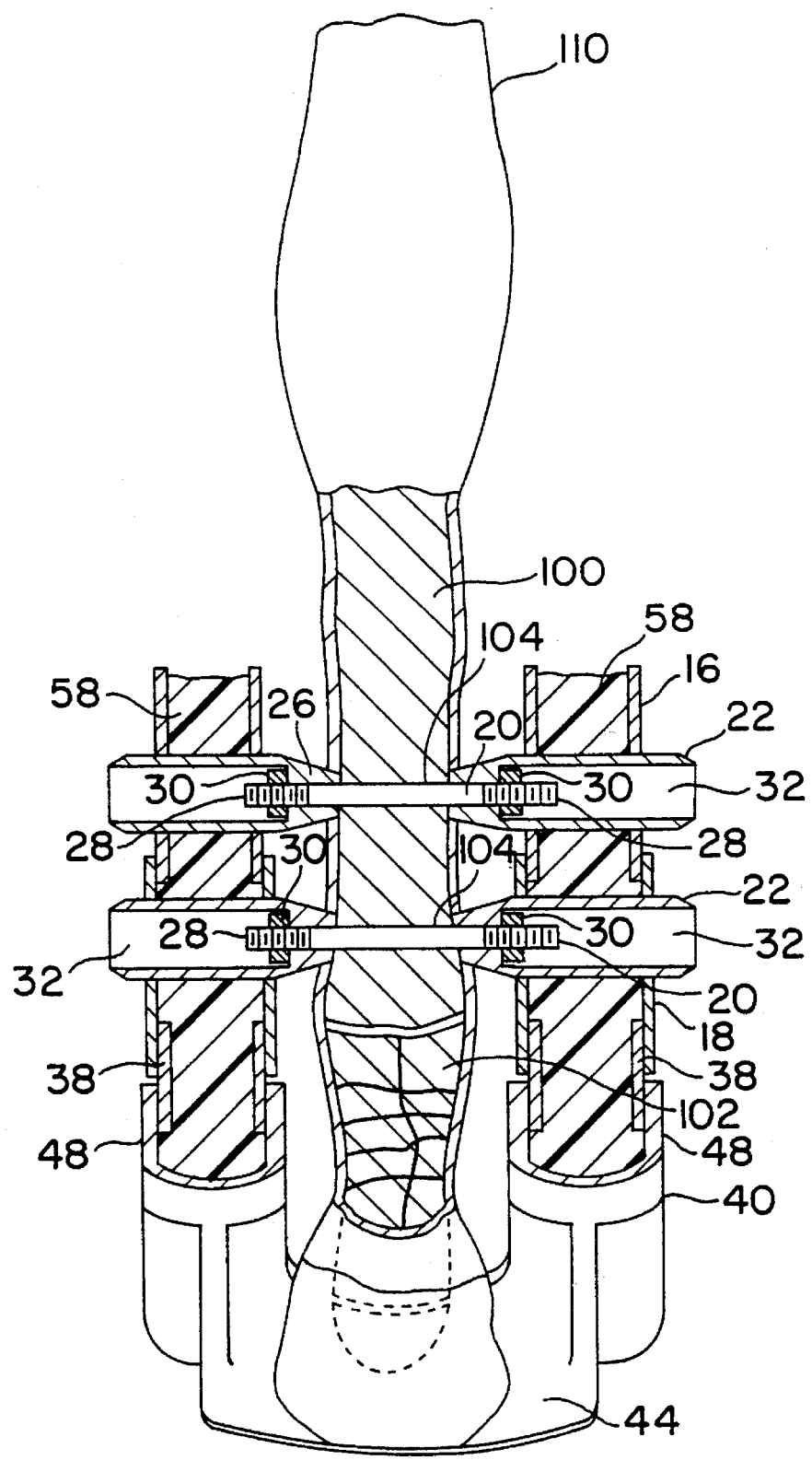
FIG. 7 is a partial cross-sectional view of the external fixation device of the present invention.

FIG. 7 shows the injured leg 110 of a horse. As can be seen, distal (or injured) bone 102 is fractured into many pieces, as is commonly the case in horses. Bone 100, proximal injured bone 102 is intact and unharmed. Intact bone 100 can therefore bear the entire weight of the animal. Normally, this bone would transfer weight to distal bone 102. However, in its injured condition, injured bone 102 cannot bear any weight. Accordingly, the device of the present invention will transfer the weight of the animal past the injured bone to the ground.

In most external fixation devices, there must be some contact with the bone of the patient to transfer force from the bone to the device. In this case, transfixation pins 20 provide this contact. Holes 104 are drilled into intact bone 100, and transfixation pins 20 are inserted. Holes 104 should be of such a diameter that there is no clearance between transfixation pins 20 and holes 104. In this way, there can be maximum area of contact between transfixation pins 20 and holes 104 to transfer weight, thus minimizing stress points in the bone. Excess stress at the transfixation pin and bone interface can cause bone loss, contributing to stress concentration in both the transfixation pin and the bone. Of course, excess stress can also cause bone failure or transfixation pin bending or failure. Thus minimization of stress in both the transfixation pin and bone is highly desirable.

In the situation shown in FIG. 7, two transfixation pins are used to support bone 100. There may be situations where three transfixation pins may be needed for support. This could be easily accomplished with the present invention, by simply adding another transfixation pin and modifying slightly the configuration of the supporting superstructure. In placing pins 20, it is preferable to divide bone 100 into thirds and place one pin between the distal and middle thirds and one pin between the middle and proximal thirds.

In the past, transfixation pins 20 have been threaded through the portion of the transfixation pin which passes through bone 100. This helps the transfixation pin hold the bone. In the present invention, this is unnecessary, although a threaded pin of the appropriate type could be used. Further, prior fixation devices have secured pins 20 to a supporting device at a point some distance from bone 100. The stress placed on pin 20 increases geometrically as the distance from bone 100 increases. Therefore, to minimize stresses on pin 20, it is desirable to minimize the distance from bone 100 to a supporting superstructure.

Alternatively, pin 20 could be made larger and more able to handle the stresses placed upon it. However, as previously explained, this decreases the strength of the surrounding bone and is therefore undesirable. To avoid removing too much material from bone 100, pin 20 should be less than about one-third of the diameter of bone 100. Preferably, pin 20 should be about 30% of the diameter of bone 100. In this case, three-eights inch (9.6 millimeter) pins were used. Of course, pins 20 should be made from any suitable, biocompatible material, including surgical grade stainless steel. Particularly, 316 surgical stainless steel has been used with success.

Figure 4:
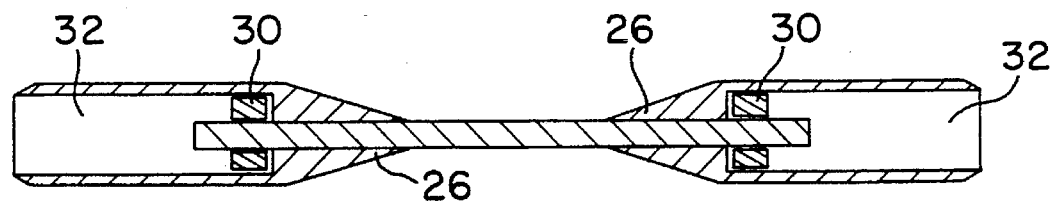
FIG. 4 is a cross-sectional view of the transfixation pin and support member of the present invention taken along line IV—IV of FIG. 3.
Figure 5:
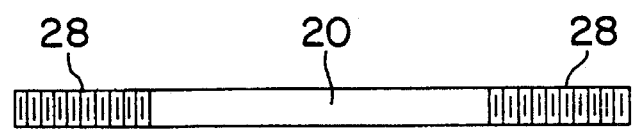
FIG. 5 is a plan view of the transfixation pin of the present invention.

To minimize the distance between bone 100 and a support for pin 20, pin supports 22 have been developed. Pin supports 22 can more easily be seen in FIGS. 3 and 4. Pin supports 22 are generally cylindrical in shape with a conical end 24. Through the center of each pin support 22 is a hole 26. This hole receives pin 20. Therefore, hole 26 should have a very tight clearance. As shown in FIG. 5, pin 20 has threads 28 on each end. Unlike prior art pins, these are not self-tapping threads intended to bite into bone 100. Rather threads 18 are machine threads designed to accept nuts 30. When pins 20 are inserted through holes 26 into pin supports 22, threads 28 protrude into a hollowed out inner portion 32. Nuts 30 are then placed on pins 20 and tightened.

To minimize stress it desirable to minimize the distance between bone 100 and a support for pin 20, as previously explained. Accordingly, nuts 30 are generally tightened until pin supports 22 contact bone 100. Thereafter, nuts 30 are tightened further to place pins 20 under tension, which provides a more stable system, resistant to plastic deformation and failure.

Figure 6:
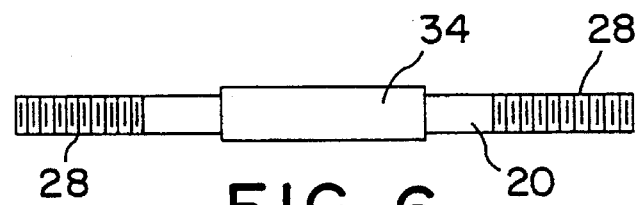
FIG. 6 is a plan view of an alternative transfixation pin according to the present invention.

In some cases, it may be undesirable to have pin supports 22 abut bone 100 (e.g. if bone 100 is slightly damaged or diseased). In this case, an alternative pin configuration show in FIG. 6 can be used. In this alternative configuration, pin 20 has a center section 34 which is larger than the remainder of pin 20. Specifically, since the size of the portion of the pin which passes through bone 100 is limited by the size of bone 100, the ends of pin 20 have a smaller diameter than center section 34. Holes 26 in pin supports 22 are then drilled slightly smaller to accommodate the reduced pin diameter. When nuts 30 are placed on pins 20 and tightened, pin supports 22 abut center section 34. Further tightening of nuts 30 will place pin 20 in tension through its middle, but pin supports will not contact bone 100.

The length of the center section 34 of pin 20 will vary depending of the diameter of the intact bone. Generally, pin supports should be proximate intact bone 100, generally within 1 inch thereof, preferably within ½ inch thereof, and most preferably within ⅛ inch thereof. Of course, as explained above, it is most desirable to have pin supports 22 in contact with intact bone 100. Therefore, it would be desirable to have available several pins having center sections of different length for use in applying the device of the present invention.

It should be noted that pin supports 22 should have hollow portions 32 of sufficiently large diameter to allow the use of a socket wrench to tighten nuts 30. Further, it would be very undesirable for nuts 20 to become loose before injured bone 102 heals. Accordingly, stop nuts should be used for nuts 20. Stop nuts are commonly known in the art and are nuts which include a plastic ring which passes over the threads of pin 20. The plastic ring provides high friction against threads 28, preventing accidental loosening of nuts 20. Any conventional method for preventing loosening of nuts 20 may also be used including lock washers, etc.

Figure 1:
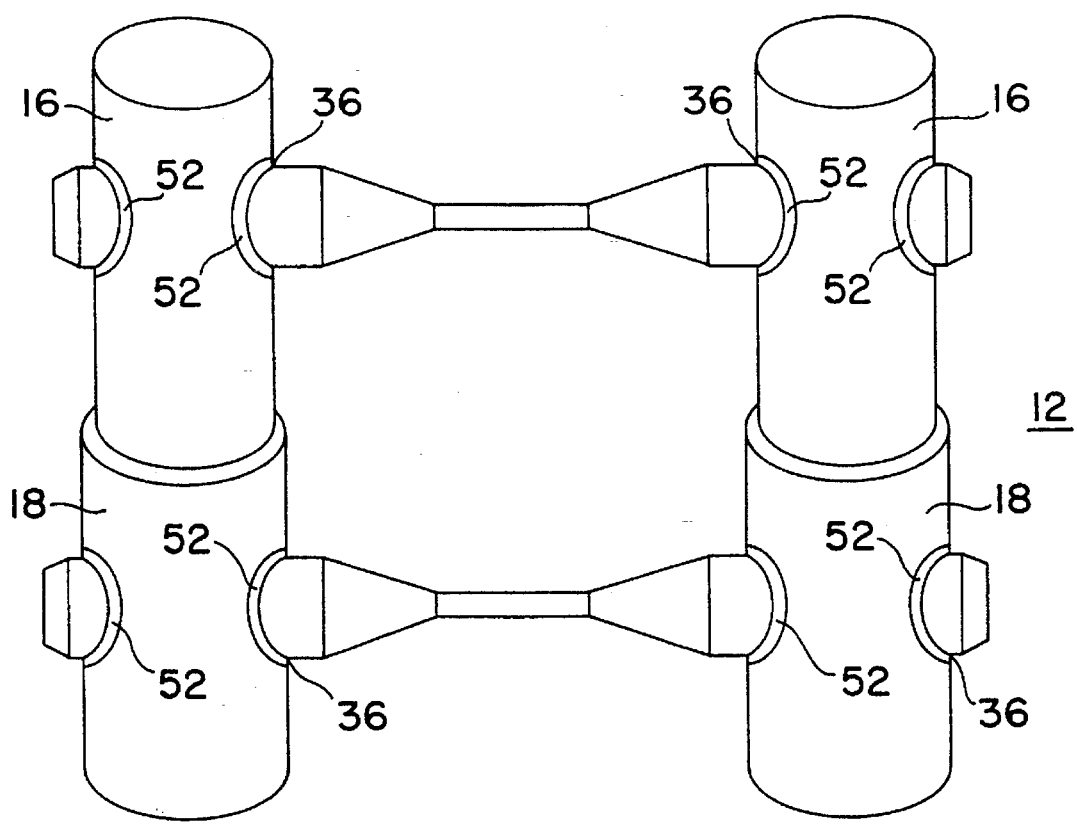
FIG. 1 is a front view of the upper portion of the superstructure of the external fixation device of the present invention.
Figure 2:
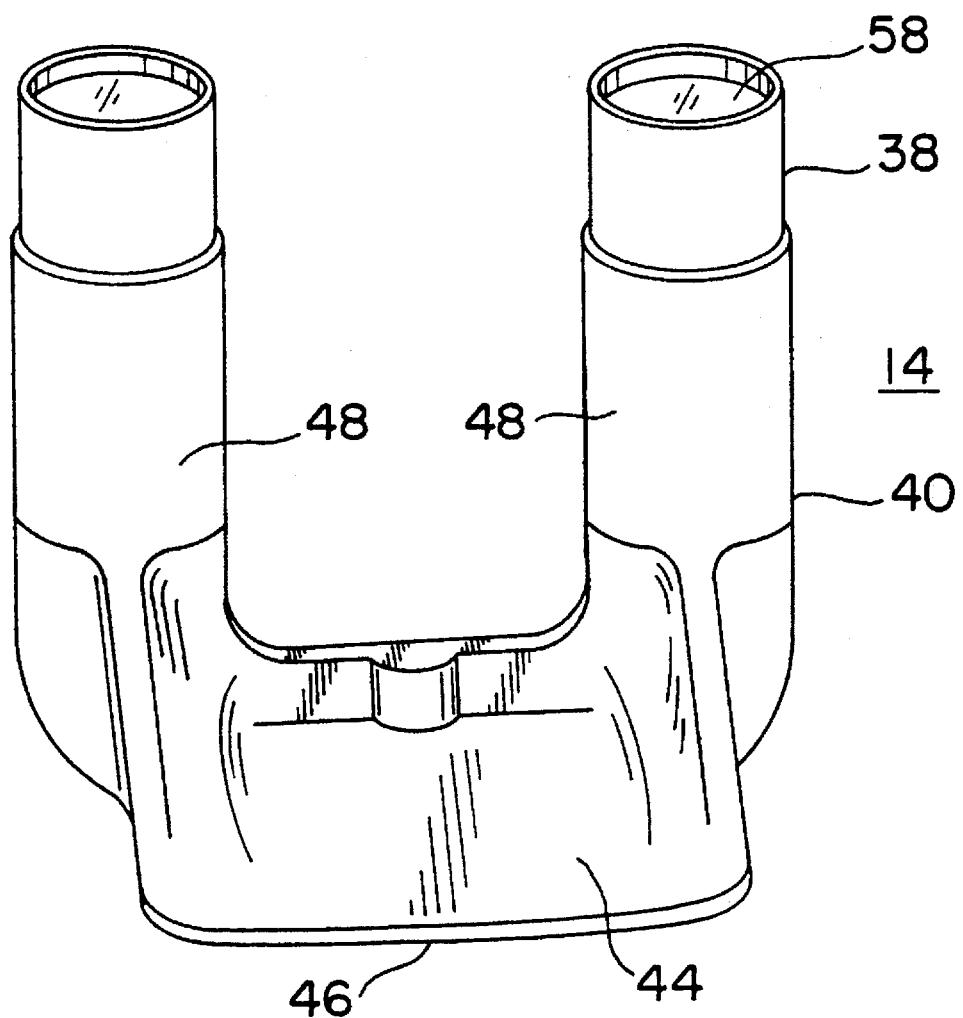
FIG. 2 is a perspective view of the lower portion of the superstructure of the external fixation device of the present invention.

Referring now to FIGS. 1, 2, and 7, superstructure 10 comprises an upper section 12 shown in FIG. 1 and a lower section 14, shown in FIG. 2. Upper section 12 essentially comprises only four hollow rigid tubes (which will later be filled with a polymeric resin), two upper tubes 16 and two lower tubes 18. Each tube has a hole 36 therethrough which extends through both sides of each tube. Upper tubes 16 should fit closely but easily inside of lower tubes 18. These tubes may be made of any rigid material including without limitation PVC or other plastic, hard rubber, aluminum, brass, copper, steel or other metals, or even paperboard. It is only required that they are sufficiently rigid to hold a resinous filling until the resin has set, as will be explained presently.

Lower section 14 comprises a base tube 38 and a base 40. Base 40 includes an upper surface 44 and a sole 46, and hollow cylindrical extensions 48. Base tubes 38 fit into cylindrical extensions 48. Once assembled, base tubes 38 and cylindrical extensions 48 can be filled with resin, or such resin can be withheld until the entire superstructure is assembled. FIG. 2 shows lower portion 14 having base tubes 38 and cylindrical extensions 48 filled with a resin 50.

Like upper tubes 16 and lower tubes 18, base tubes 38 can be formed of any suitable material. This is not the case for base 40. Base 40 will bear the weight of the animal directly, and must therefore be formed from a suitable strong (and preferably lightweight) material. Cast aluminum (or aluminum alloy) is suggested, however cast iron or machined materials can also be used. It is also contemplated that a strong plastic may also be suitable depending on the weight of the animal to be treated. It should be kept in mind that the thickness of base 40 will add length to the limb of the animal. Accordingly, this thickness should be minimized to avoid any problems occasioned by having two limbs of differing length, even for a relatively short time period. This can be compensated for as necessary in a horse for example by shoeing the horse's remaining hooves.

Once pin 20 is in place in bone 100, and pin supports 22 have been installed and tightened, the pin supports must be secured in superstructure 10 which will allow the transfer of the weight of the animal to the ground. Upper tubes 16 and lower tubes 18 are assembled and slid over pin supports 22. In order to facilitate a seal between pin supports 22 and upper tubes 16 and lower tubes 18, rubber grommets 52 may be installed. It is contemplated that pins 20 will be placed about 3–4 inches apart, in which case holes 36 should be 1 ½ to 2 inches from the ends of upper and lower tubes 16 and 18. This provides for a ¼ to ½ inch overlap between upper and lower tubes 16 and 18. More overlap is acceptable, as is less, providing a seal between the tubes can be established.

Generally, once upper and lower tubes 16 and 18 are assembled, the joint is wrapped with adhesive tape or other sealant. This seals any gap between the tubes and prevents leakage of resin prior to hardening. After assembly of upper superstructure portion 12, lower superstructure portion 14 (which has been previously assembled) is positioned. This is accomplished by sliding base tubes 38 into lower tubes 18 until upper surface 44 of base 40 contacts the distal end of the limb. In the case of a horse, upper surface 44 of base 40 can be affixed directly to the bottom of the hoof by any suitable means. If gluing is desired, a suitable fast-setting acrylic adhesive may be used. Alternatively, base 40 can be nailed or screwed into the horse's hoof. An intermediate plate can also be secured to the horse's hoof and to base 40 if desired.

Figure 3:
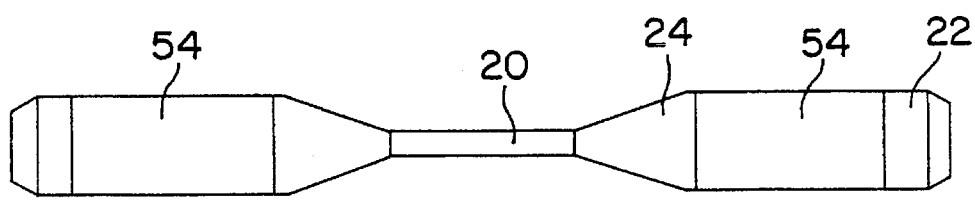
FIG. 3 is a plan view of the transfixation pin and support member of the present invention.

The joint between lower tubes 18 and cylindrical extensions 48 is then sealed with tape (or other sealant). Finally the limb is placed in a vertical upright position and the entire volumes within tubes 16, 18, and 38 as well as cylindrical extensions 48 are filled with a strong, fast setting resin poured through the tops of upper tubes 16. The limb and superstructure are then maintained in this upright position until resin 52 cures. Resin 52 bonds and holds the pieces of superstructure 10 in place, including pin supports 22. To allow resin 52 to attach more firmly to pin supports 22, pin supports 22 may include a knurled or scored section 54 as shown in FIG. 3.

In order to be able to apply the device to different animals, several different sizes of parts should be available. For example, pins of differing lengths are needed for bones of differing diameters. Further, since the pin diameter should be about 30% of the intact bone diameter, pins of differing diameters should also be available. Similarly, upper and lower tubes of different lengths should be available. Alternatively, a tube may be placed intermediate upper and lower tubes 16 and 18 to adjust the device for limbs of differing lengths.

Resin 52 should be chosen carefully. Specifically, if resin 52 cures exothermically, producing heat, the resin should not get above about 50° C. or heat generated by the resin may diffuse through pin supports 22 and heat pins 20 which could burn the bone and soft tissue of the animal. Suitable resins include polymeric melts which solidify on cooling as well as pliant curable prepolymers and extended or filled polymeric or polymerizable monomeric or polymeric materials. Such materials include the class of thermosetting resins. Among this class, epoxy, urethane, phenolic, and polyester resins exhibit cure times and temperatures which make them desirable. The permissible cure time of the resin will vary with the mammalian species. Suitable resins include Ultracast FR-1177 available from Fiber-Resin Corp, 170 W. Providencia Ave., Burbank, Calif. 91503, and TC-880 A/B, TC-806 A/B and TC-804 A/B available from BJB Enterprises of 13912 Nautilus Drive, Garden Grove, Calif. 92643.

The resins of choice are generally low viscosity materials prior to curing. It is for this reason that the joints between tubes 16 and 18 and base 40, as well as between tubes 16 and 18 and pin supports 22, must be sealed with adhesive tape. Otherwise, the low viscosity resin will run out the joints before curing. Upon curing, the resin, in conjunction with tubes 16 and 18, and base 40, forms a rigid superstructure consisting of two rigid cylindrical members, each connected on opposite sides of a base. This rigid superstructure then holds the intact bone, through pins and pin supports, to the base of the superstructure.

Once the resin is sufficiently cured, the animal can be revived. The injured bone of the animal normally heals to the point where the external fixation device should be removed in 8 to 12 weeks. Thereafter, a traditional cast or other form of support may be necessary after removal of the device of the present invention, while the bones regain full strength. Removal of the device must, as a practical matter, be made destructively, by cutting base 40 and removing nuts 30, which will allow the two halves of the superstructure to be slid off pins 20. Any other method of cutting superstructure 10 can also be used.

It is understood that various other modifications will be apparent to one skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed:

1. An external skeletal fixator for treating an injured animal limb having a proximal end and a distal end, the fixator comprises:

a plurality of transfixation pins adapted to transfix bone at separated sites along the limb proximal the injury and pass completely through and protrude from the limb;

elongated pin supports, each having a longitudinal axis, for supporting said transfixation pins proximate said bone, on both sides of said bone, each said pin support having a bore therethrough along said longitudinal axis for accepting one said transfixation pin; and a base for attachment distal to the distal end of the limb in order to bear at least a portion of the weight of the animal;

means for rigidly connecting said pin supports to said base and for transferring said portion of the weight of the animal to said base.

2. The external skeletal fixator of claim 1 wherein said pin supports are adapted to be fastened within ½ inch of an outer surface of said bone.

3. The external skeletal fixator of claim 2 wherein said pin supports are adapted to be fastened within ⅛ inch of said outer surface.

4. The external skeletal fixator of claim 3 wherein said pin supports are adapted for contact with said outer surface.

5. The external skeletal fixator of claim 2 wherein at least one of said transfixation pins includes a center section having a larger diameter than the remainder of said transfixation pin.

6. The external skeletal fixator of claim 1 wherein said pins have two ends and include machine threads on said two ends thereof.

7. The external skeletal fixator of claim 6 wherein said pins project through said pin supports and are secured thereto using nuts.

8. The external skeletal fixator of claim 1 wherein said means for rigidly connecting said pin supports to a base comprises two rigid columns.

9. The external skeletal fixator of claim 8 wherein said two rigid columns each comprise a rigid polymeric resin.

10. The external skeletal fixator of claim 9 wherein said polymeric resin is a thermosetting resin.

11. The external skeletal fixator of claim 10 wherein said thermosetting resin is selected from the group consisting of epoxy, urethane, phenolic, and polyester resins.

12. The skeletal fixator of claim 1 wherein said pin supports extend inwardly, in the direction of said bone, from said means for rigidly connecting said pin supports to said base.

13. The skeletal fixator of claim 1 wherein said pin supports comprise hollow members having a cylindrical section and a conical section.

14. The skeletal fixator of claim 12 wherein the cross sectional area of said pin supports, taken perpendicular to the length of said transfixation pin, decreases as the distance from said bone decreases.

15. A method for treating an injured animal limb has been inserted after limb. comprising:
  providing a plurality of transfixation pins, a plurality of elongated pin supports, each having a longitudinal axis, and a base for attachment distal to the distal end of the limb in order to bear at least a portion of the weight of the animal;
  transfixing said plurality of transfixation pins through an intact bone proximal the injury at separated sites along said bone such that said transfixation pins protrude from the limb;
  connecting each said pins to a pair of said pin supports for supporting said transfixation pins proximate said bone by inserting each transfixation pin through a hole bored into each said pin support along said longitudinal axis; and
  rigidly connecting said pin supports to said base through a superstructure.

16. The method of claim 15 including, after the step of connecting said pins to said pin supports for supporting said transfixation pins proximate said bone, the further step of affixing a distal end of said limb to said base.

17. The method of claim 15 wherein the step of rigidly connecting said pin supports to said base through a superstructure comprises:
  providing a pair hollow tubes for each said pair of pin support, each said tube having a hole formed therethrough, transverse to a longitudinal axis of the tube;
  inserting each of said pin support through said transverse holes in said pair of hollow tubes;
  coaxially aligning and joining the ends said hollow tubes, one from each said pair, to one another to form a first hollow cylinder, and coaxially aligning and, joining the ends of the other of each said pair of hollow tubes to one another to form a second hollow cylinder;
  coaxially aligning and joining one end of each of said two hollow cylinders to two base tubes protruding from said base;
  mixing a resinous polymerizable material to initiate polymerization;
  filling said hollow cylinders and base tubes with said mixed polymerizable resinous material to fill said tubes and cylinders and thereby surround and secure said pin supports inserted therethrough; and
  allowing said resinous material to polymerize and form two rigid cylindrical resinous masses contained within said cylinders and surrounding and securing said pin supports.

18. An external skeletal fixator kit for treating an injured animal limb having a proximal and distal end comprising:
  a plurality of transfixation pins adapted to transfix bone and protrude therefrom;
  elongated pin supports, each having a longitudinal axis and a bore therethrough along said axis, adapted to support said transfixation pins in said bore proximate an intact animal bone;
  a base for attachment distal to the distal end of the limb in order to bear at least a portion of the weight of the animal; and
  means for rigidly connecting said pin supports to said base.

19. The kit of claim 18 wherein said means for rigidly connecting said pin supports to said base comprises:
  a plurality of hollow tubes adapted for assembly into two hollow cylinders, said tubes including holes for receiving said pin supports; and
  sufficient polymerizable resinous material to fill said hollow tubes.

20. The kit of claim 18 wherein said plurality of transfixation pins each have a center section having a larger diameter than the remainder of said transfixation pin.

* * * * *

UNITED STATES PATENT AND TRADEMARK OFFICE
CERTIFICATE OF CORRECTION

PATENT NO. : 5,578,041
DATED : November 26, 1996
INVENTOR(S) : Nash et al.

It is certified that error appears in the above-indentified patent and that said Letters Patent is hereby corrected as shown below:

At column 7, lines 43-44, delete "has been inserted after limb." and insert --having a proximal and distal end--.

At column 8, line 13, after "said" (first occurrence), insert --pair of--.

Signed and Sealed this

Twentieth Day of May, 1997

Attest:

BRUCE LEHMAN

Attesting Officer

Commissioner of Patents and Trademarks